(12) United States Patent
Pitaoulis

(10) Patent No.: US 11,304,773 B2
(45) Date of Patent: Apr. 19, 2022

(54) DISPOSABLE RADIAL ACCESS CATHETERIZATION SLEEVE

(76) Inventor: Christos Pitaoulis, Brooklyn, NY (US)

( * ) Notice: Subject to any disclaimer, the term of this patent is extended or adjusted under 35 U.S.C. 154(b) by 0 days.

(21) Appl. No.: 13/273,796

(22) Filed: Oct. 14, 2011

(65) Prior Publication Data

US 2012/0097176 A1  Apr. 26, 2012

Related U.S. Application Data

(60) Provisional application No. 61/394,815, filed on Oct. 20, 2010.

(51) Int. Cl.
*A61B 46/27* (2016.01)
*A61B 46/20* (2016.01)

(52) U.S. Cl.
CPC ........ *A61B 46/27* (2016.02); *A61B 2046/205* (2016.02)

(58) Field of Classification Search
CPC ... A61B 46/00–40; A61B 46/20; A61B 46/27; A61B 2046/205; A61M 25/02–04; A61M 25/00; A61F 13/00–00085; A61F 13/02–0266; A61F 13/10–108; A61F 2013/00089–00357; A41D 13/08–088
USPC ........... 128/846, 849, 851–856; 602/60, 62; 2/16, 21, 66, 158, 159, 160, 910, 917
See application file for complete search history.

(56) References Cited

U.S. PATENT DOCUMENTS

| | | | | |
|---|---|---|---|---|
| 3,424,153 A * | 1/1969 | Lewis, Jr. | | 128/856 |
| 3,707,964 A * | 1/1973 | Patience et al. | | 128/856 |
| 3,769,971 A * | 11/1973 | Collins | | 128/856 |
| 3,989,040 A * | 11/1976 | Lofgren | | A61B 46/27 |
| | | | | 128/856 |
| 4,470,410 A * | 9/1984 | Elliott | | A61M 5/52 |
| | | | | 128/877 |
| 4,582,508 A | 4/1986 | Pavelka | | |
| 4,633,863 A | 1/1987 | Filips et al. | | |
| 4,745,915 A * | 5/1988 | Enright et al. | | 128/853 |
| 4,911,151 A * | 3/1990 | Rankin et al. | | 602/3 |
| 5,010,617 A * | 4/1991 | Nelson | | A47L 23/10 |
| | | | | 15/227 |
| 5,178,162 A * | 1/1993 | Bose | | A61B 46/27 |
| | | | | 128/849 |
| 5,238,010 A | 8/1993 | Grabenkort et al. | | |
| 5,342,286 A * | 8/1994 | Kelly et al. | | 602/3 |
| 5,415,642 A | 5/1995 | Shepherd | | |
| 5,437,621 A * | 8/1995 | Andrews | | A61F 13/104 |
| | | | | 2/16 |
| 5,562,107 A * | 10/1996 | Lavender | | A61F 13/0269 |
| | | | | 128/888 |
| 5,785,057 A * | 7/1998 | Fischer | | 128/846 |
| 5,807,341 A | 9/1998 | Heim | | |
| 5,975,082 A * | 11/1999 | Dowdy | | 128/849 |
| 6,014,774 A * | 1/2000 | Davey | | A41D 19/01 |
| | | | | 2/158 |
| 6,571,395 B1 | 6/2003 | Korkor | | |
| 7,058,447 B2 | 6/2006 | Hill et al. | | |

(Continued)

*Primary Examiner* — Michelle J Lee

(74) *Attorney, Agent, or Firm* — F. Chau & Associates, LLC

(57) ABSTRACT

A disposable radial access catheterization sleeve is provided for radial access catheterization. The sleeve includes a closed distal end, and open proximal end and a tubular sidewall extending between the ends. An access opening is formed in the tubular sidewall to permit access to a catheterization site on the arm of the patient.

3 Claims, 13 Drawing Sheets

(56) References Cited

U.S. PATENT DOCUMENTS

| | | |
|---|---|---|
| 7,678,092 B2 * | 3/2010 | Matloub et al. .............. 604/355 |
| 2003/0150044 A1 | 8/2003 | Hoy |
| 2007/0073227 A1 * | 3/2007 | Hewes et al. ................. 604/110 |
| 2009/0247965 A1 | 10/2009 | Williams |
| 2013/0125901 A1 * | 5/2013 | Pitaoulis ................ A61B 46/27 |
| | | 128/851 |

* cited by examiner

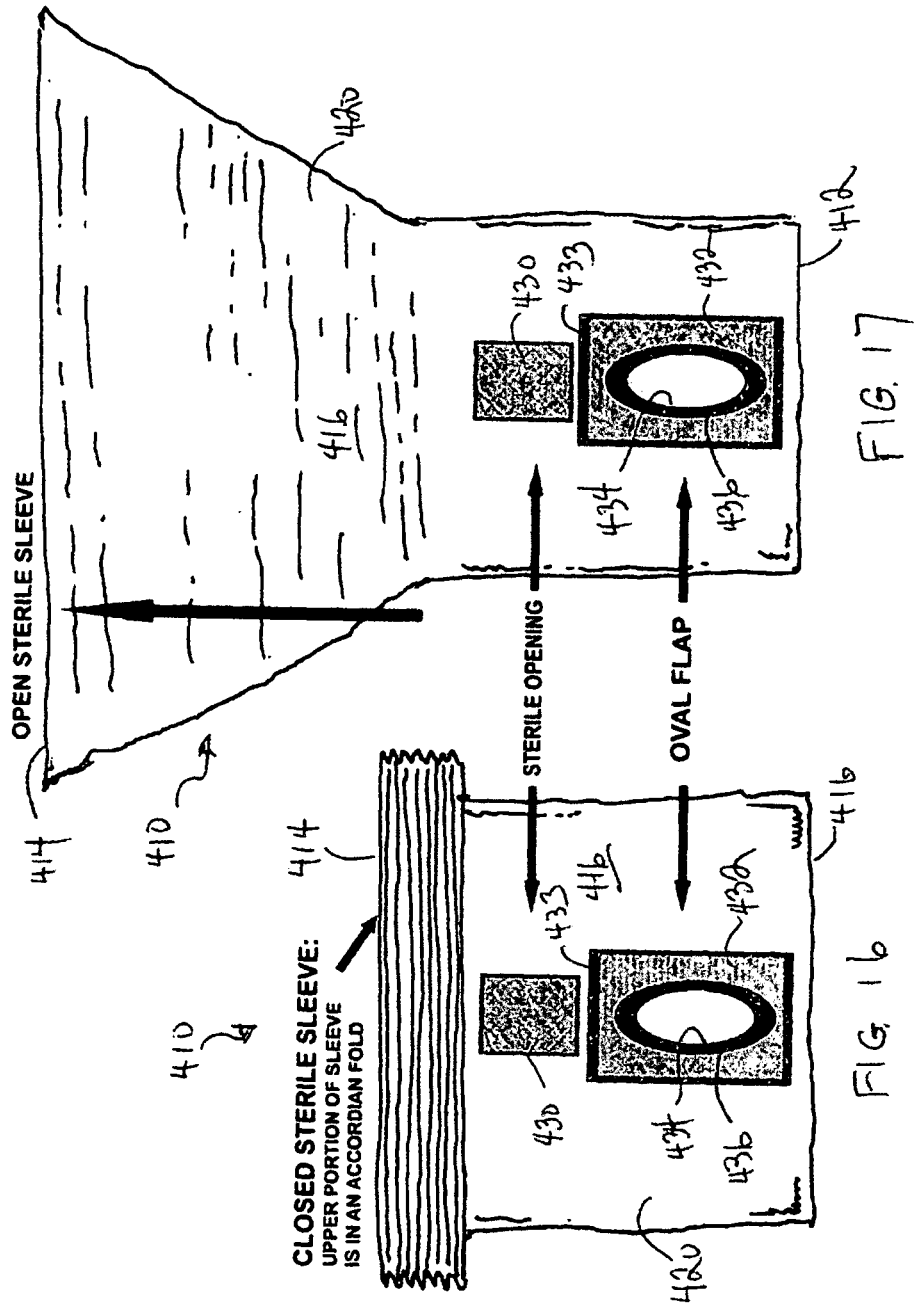

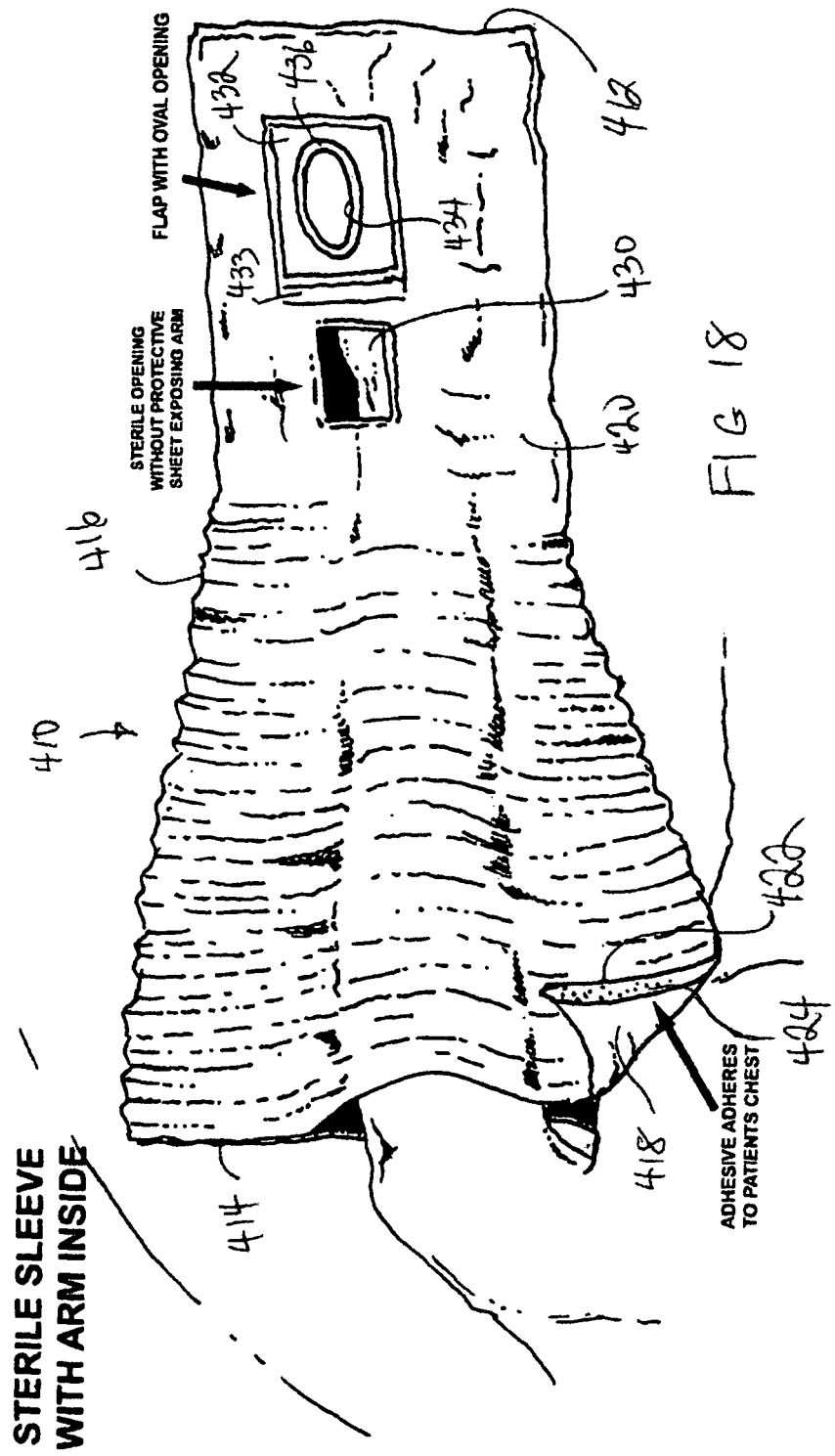

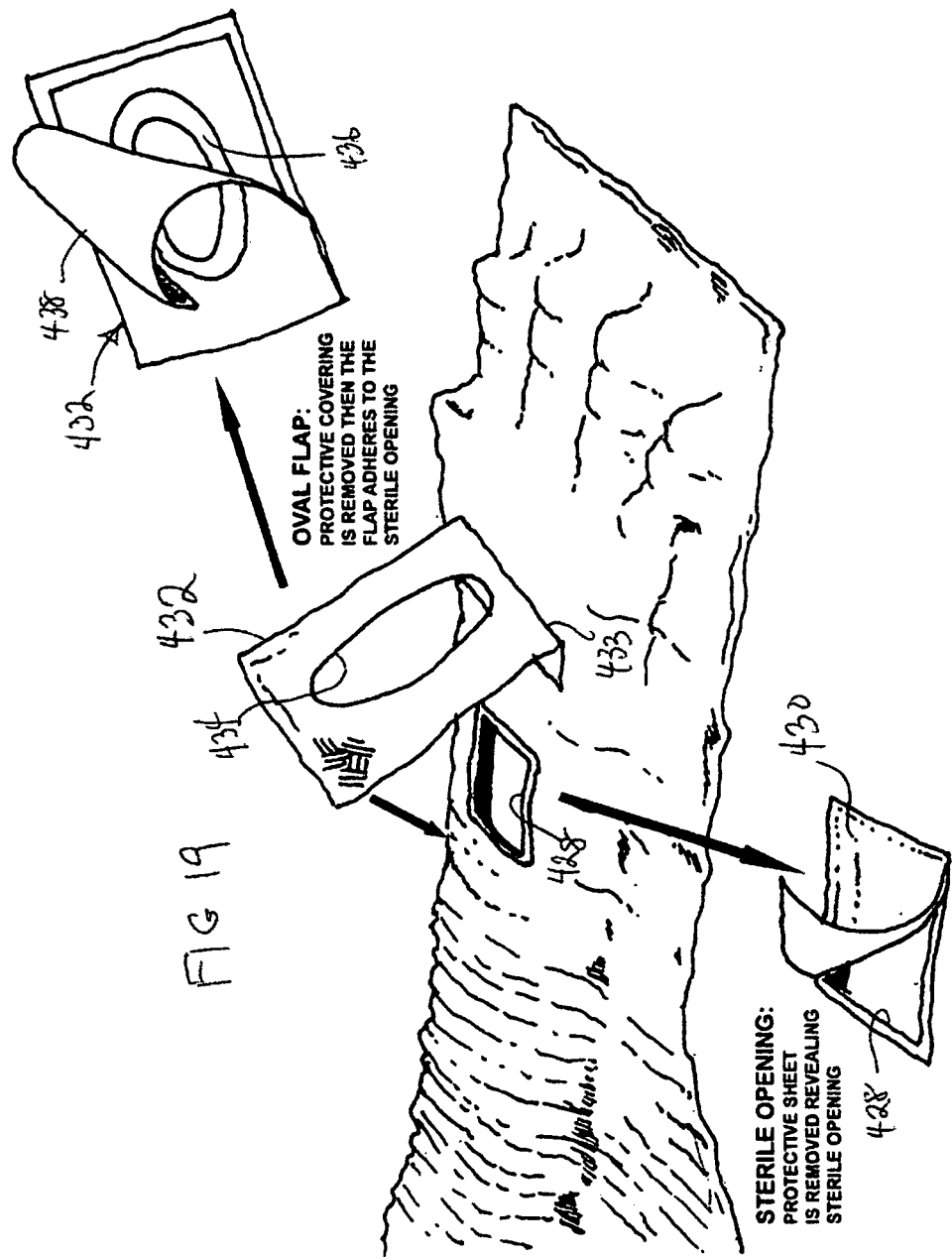

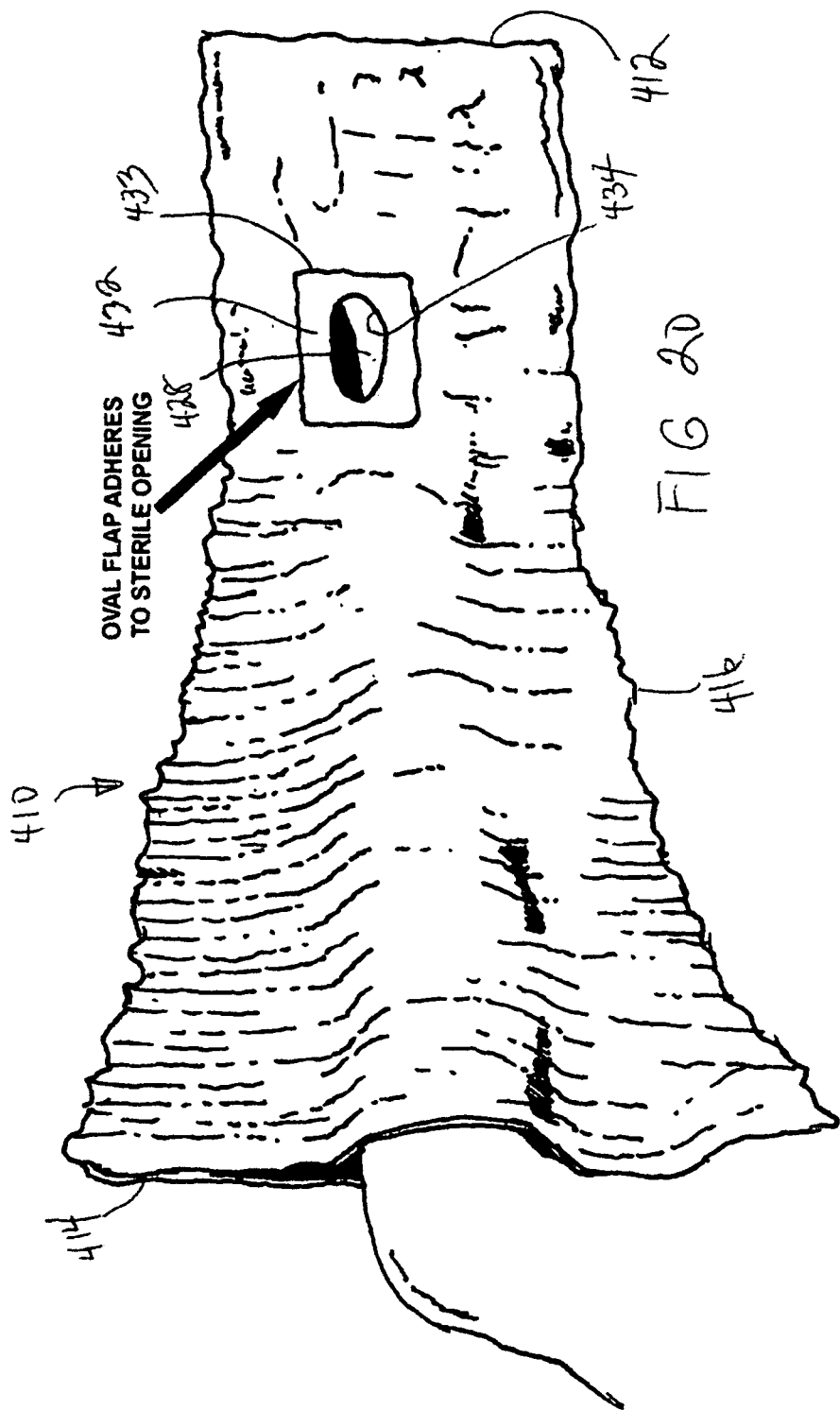

DISPOSABLE RADIAL ACCESS CATHETERIZATION SLEEVE

CROSS-REFERENCE TO RELATED APPLICATION

This application is a continuation-in-part of application Ser. No. 13/273,796, filed Oct. 14, 2011, which claims priority on U.S. Provisional Appl. No. 61/394,815 filed on Oct. 20, 2010.

BACKGROUND OF THE INVENTION

1. Field of the Invention

The invention relates to a disposable radial access catheterization sleeve that can be used to provide sterility during a surgical procedure in which the disposable radial access sleeve can be adapted to or configured to a patient's arm or wrist is accessed.

2. Description of the Related Art

Cardiac catheterization is a medical procedure that inserts a catheter into a blood vessel at a location spaced from the heart. The catheter then is advanced through the blood vessel to a location near the heart and is used to guide surgical tools or prosthetic components into the region of the heart. For example, cardiac catheterization may be used to repair a damaged section of the blood vessel or a damaged valve or to implant a graft or stent.

For many years, cardiac catheterization was carried out by accessing the femoral artery in a portion of the thigh near the groin. More recently, cardiac catheterization has been carried out by accessing a blood vessel in the wrist or forearm. Cardiac catheterization that accesses a blood vessel in the wrist area generally is referred to as radial access catheterization. Catheterization that accesses a blood vessel closer to the elbow area of the forearm generally is referred to as brachial catheterization.

A patient typically is lying prone on an operating table during a radial or brachial access catheterization procedure. The arm that will be accessed is supported on a lateral extension of the operating table. Thus, doctors and other medical personnel who will be involved in the procedure will be on the side of the patient with the arm that will be accessed and in proximity to the arm during the procedure.

Sterility is extremely important during all invasive medical procedures. Medical personnel performing the procedure take steps to scrub and/or cover parts of their body. Areas of the patient near the access or entity site must be sterilized and must be isolated from parts of the patient that are not sterilized. Areas near the entry site are likely to be shaved, scrubbed and wiped with an antiseptic solution. Sterile sheets or drapes then are placed over other areas of the patient and are taped or otherwise secured to the patient to ensure that non-sterile areas of the patient do not adversely affect areas near the entry side that have been cleaned.

Cardiac catheterization that accesses the femoral artery will sterilize areas near the access site in the upper thigh or groin area. Sterile surgical drapes then will be positioned on the operating table and over the patient to cover the torso, the leg that is not being accessed and the lower part of the leg that is being accessed. These drapes are secured to the patient and areas of these sterile surgical drapes that extend beyond the patient can be positioned conveniently on the operating table in a manner that will not interfere with the doctor and other medical personnel.

Cardiac catheterization that enters the blood vessel in the patient's forearm typically has utilized the same sterile surgical drapes that are used for cardiac catheterization that accesses the thigh. However, the size and orientation of the extension of the operating table on which the arm is supported and the size and shape of the arm complicates efforts to use traditional sterile surgical drapes. More particularly, the drapes are likely to hang over the sides of the operating table extension on which the arm is supported and are prone to being displaced. Doctors are likely to improvise arrangements of clamps, tapes and the like in efforts to hold the sterile surgical drapes in a position that permit access to the location on the patient where the blood vessel will be entered while also keeping other non-sterile areas of the patient covered and isolated from the site of the surgical entry. A patient who is undergoing cardiac catheterization also typically has a blood oxygen monitor clipped to a finger. The presence of a blood oxygen monitor on a finger of the arm that is being accessed further complicates efforts to maintain sterility at the surgical access site.

The subject invention has been developed in view of the above-described problems.

SUMMARY OF THE INVENTION

The subject invention relates to a disposable radial access catheterization sleeve that can be adapted to or configured to a patient's arm during radial or brachial access catheterization. The disposable radial access catheterization sleeve may be formed from plastic or non-woven fabric that is coated with plastic or other fluid impermeable material. The disposable radial access catheterization sleeve preferably has a closed or closable end that will be adapted to or configured cover the hand of the patient and an open end that will be adapted to or configured to extend to or slightly beyond the shoulder area. Sides of the disposable radial access catheterization sleeve may be closed permanently between the opposite ends of the sleeve. Alternatively, one side of the disposable radial access catheterization sleeve may define a closable opening, such as an opening that may be closed by an adhesive material. One or more tabs may be provided at or near the open end of the sleeve to facilitate gripping of the sleeve as the sleeve is being adapted to or configured to be positioned over the patient's arm. The tab also will define areas of the disposable radial access catheterization sleeve that will be gripped initially by a health care professional when the sleeve is being removed from its sterile package and will be held by the health care professional during mounting, adapting or configuring over the patient's arm. The tab or tabs also can be used for anchoring and configuring a sleeve more securely near the shoulder. For example, the tabs can define a convenient location for applying adhesive tape to secure the open end of the disposable radial access catheterization sleeve to the shoulder area of the patient or can be engaged by a clamp to secure the open end of the disposable radial access catheterization sleeve to structure on or near the operating table.

In a particularly preferred embodiment, adhesive may be applied entirely around the open end of the sleeve and/or an open side of the sleeve. The adhesive may be covered by a release lining or layer that can be removed after the sleeve is positioned properly over the arm of the patient. The adhesive enables the health care professional to securely but removably attach the open end of the sleeve directly to the patient's skin to ensure that sterility will be maintained entirely along the arm of the patient and to maintain proper positioning of the sleeve during the procedure. The adhesive also may be used to secure one region of the sleeve to another region of the sleeve. For example, a strip of adhesive may extend along a free side edge of the sleeve and may be secured to an opposed side area of the sleeve to close the sleeve between the end of the sleeve that will cover the hand and the end of the sleeve that will be near the shoulder. Still further, adhesive may be provided to form a closure around the hand and/or to secure an area of the sleeve near the wrist or forearm to the closure for the hand.

The sleeve may further include an oxygen saturation monitor incorporated into the closed el id of the sleeve and at a position where the fingers will be located. The oxygen saturation monitor can be clipped or otherwise mounted onto the patient's finger after the sleeve has been positioned properly over the patient's arm. Appropriate connections to signal carrying means, such as cables, can be connected to the oxygen saturation monitor at a connection that is accessible from the outside of the sleeve. Thus, the oxygen saturation monitor can be positioned as part of the mounting of the sleeve to obtain sterility during the surgery.

Importantly, the sleeve includes at least one area that can be opened selectively to expose the area on the arm that will be catheterized. The opening may be defined by a generally U-shaped cut that extends at least partly through the plastic or plastic coated non-woven fabric to form a flap that can be opened a desired amount to expose the skin of the arm. An adhesive can be applied to the interior surface of the sleeve at locations surrounding the U-shaped cut so that a sleeve can be secured to the skin of the patient generally around the perimeter of the area where the catheter will access the blood vessel. As an alternative, the sleeve can have a single linear cut that permits areas on opposite sides of the cut to be separated from one another for accessing the skin of the patient. The linear cut preferably extends from the area of the wrist to the area of the elbow. Adhesive can be applied to the inner surface of the sleeve on opposite sides of the cut so that the plastic or fabric of the sleeve can be secured to the patient, thereby enhancing sterility at the location where the catheter is inserted into the blood vessel. Still further, the opening may be a generally circular opening covered by a repositionable adhesive-backed flap that can be partly removed from the sleeve for accessing the skin of the patient for catheterization.

A further alternate sleeve may include a sterile opening that is covered in a sterile manner by a protective sheet that is selectively removable from the sleeve to expose the skin of the patient's arm. A flap may be mounted hingedly to the sleeve in proximity to the sterile opening and the removable protective sheet. The flap may include a small access opening and adhesive at least partly surrounding the access opening. A protective release layer may be removably attached to the flap for covering the access opening and covering and protecting the adhesive around the access opening. The protective sheet may be removed after the sleeve is mounted on the patient to expose the skin of the patient near the blood vessel that will be entered. The release layer then may be removed from the flap and the flap may be rotated relative to the sleeve to overlie the sterile opening in the sleeve that had been covered by the protective sheet. The adhesive that surrounds the access opening in the flap may be secured to the outer surface of the sleeve near the sterile opening or adhered to the skin of the patient near the sterile opening.

The sleeve can be packaged and used with a small sterile sheet that can be positioned at least partly over the slit or other access opening in the sleeve. The additional small sterile sheet optionally can be used to limit the size of the access opening in the sleeve. Alternatively, the sleeve can have an extension that functions as a drape for covering areas adjacent to the arm that will be catheterized.

The subject invention provides several significant advances over the prior art. More particularly, the invention provides a small neat sterile enclosure that avoids the above-described problems associated with large sterile drapes that must be secured over and attached to the operating table extension for the arm. The absence of drapes hanging from the operating table extension improves safety and efficiency. Additionally, the sleeve of the subject invention will not be dislodged accidentally from the patient, thereby ensuring a highly sterile environment. Furthermore, the sleeve is easy to position by one person and does not require a complex assembly of clamps or the like.

The sleeve of the subject invention also is well suited for placement in a small sterile package that can be opened immediately prior to mounting the sleeve. The open end of the sleeve can be collapsed toward the closed end in much the manner of an accordion. The health care professional merely needs to grab the tabs near the open end of the sleeve to remove the sleeve from the package. The closed end of the sleeve then merely is positioned over the patient's hand and the tabs are pulled toward the shoulder to position the sleeve over the arm of the patient. In other embodiments, the sleeve can have top and bottom panels hingedly connected to one another along eightfold area that extends from the closed end of the sleeve to the open end. The bottom panel can be positioned under the arm of the patient and the top panel can be folded over the arm. Areas of the top and bottom panels opposite the failed area can be secured to one another by adhesive tape. With these and other embodiments described herein, the sleeve can be removed from its package, positioned and mounted on the patient efficiently and quickly.

The sleeve is well suited to the size of the area that needs to be protected in a sterile manner. There is no need for large sterile drapes, and hence costs remain low.

BRIEF DESCRIPTION OF THE DRAWINGS

FIG. 16 is a top plan view of a sleeve in accordance with a fifth embodiment of the invention showing the sleeve in a collapsed condition for packaging prior to use.

FIG. 17 is a top plan view of the sleeve of FIG. 16 showing the sleeve in an expanded condition after removal from its sterile package.

FIG. 18 is a perspective view showing the sleeve of FIGS. 16 and 17 as initially mounted on the patient.

FIG. 19 is a perspective view showing the sleeve of FIGS. 16-18 mounted on the patient after removal of the protective sheet from the sterile opening and during the positioning of the flap near the sterile opening.

FIG. 20 is a perspective view similar to FIGS. 18 and 19 and showing the flap secured in its final position in proximity to the sterile opening.

DETAILED DESCRIPTION OF THE PREFERRED EMBODIMENTS

Figure 1:
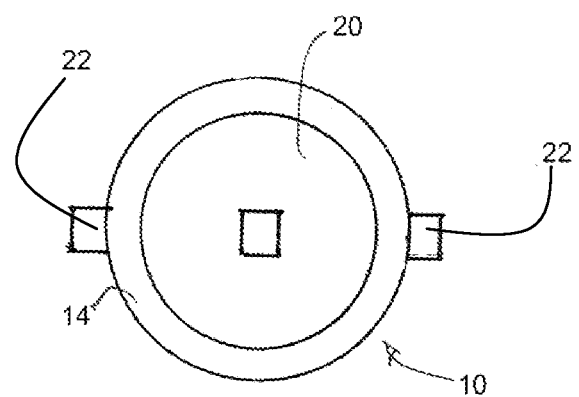
FIG. 1 is a top plan view of a sleeve in accordance with a first embodiment of the subject invention in a collapsed state.

A radial or brachial access catheterization sleeve in accordance with a first embodiment the subject invention is identified generally by the numeral 10 in FIGS. 1-3 and 5-7. The sleeve 10 is formed from a flexible plastic, such as polypropylene, or alternatively from a flexible nonwoven fabric or paper material that is coated with plastic or other fluid impermeable material and may be formed from materials currently used for disposable medical or surgical drapes. The sleeve 10 of the first embodiment has a closed end 12, an open end 14 and a generally collapsed or collapsible tubular side wall 16 extending between the ends.

Figure 2:
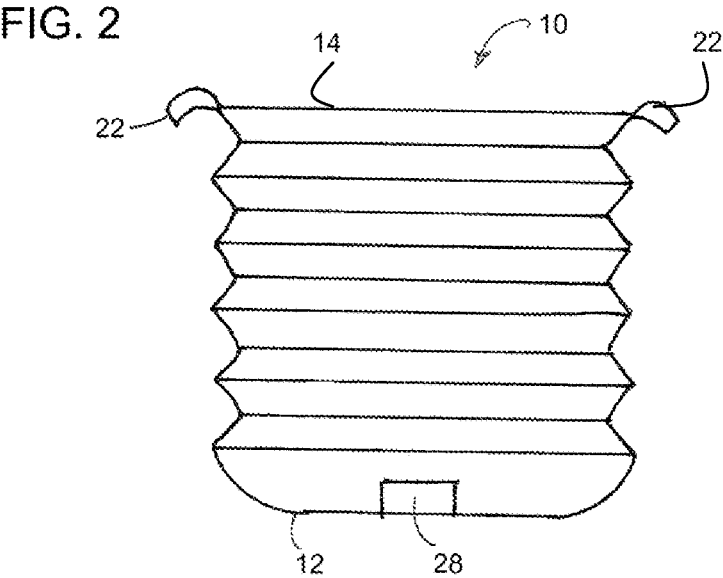
FIG. 2 is a side elevational view of the sleeve in a partly expanded state.
Figure 3:
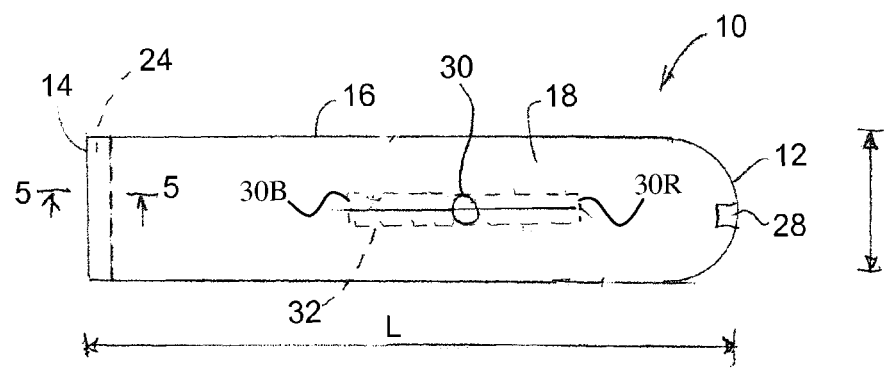
FIG. 3 is a top plan view of the sleeve in a fully expanded state.

The sleeve 10 preferably is packaged in a sterile enclosure, such as a poly-paper laminated enclosure (not shown), and will be opened and accessed immediately prior to a procedure in the operating room or other medical facility. For convenient storage, the sleeve is collapsed in a generally accordion shape so that the open end 14 nests on the closed end 12. The sleeve 10 has an outer surface 18, as shown most clearly in FIGS. 3 and 5, and an opposite inner surface 20, as shown most clearly in FIGS. 1 and 5. With reference to FIG. 3, the sleeve 10 has an overall length from the closed end 12 to the open end 14 that will permit the sleeve to extend over the arm of a patient so that the closed end 12 covers the hand of the patient and so that the open end 14 is in proximity to the shoulder of the patient. In a preferred embodiment, the sleeve 10 will have a length of approximately 90 cm. As shown in FIGS. 1 and 2, tabs 22 project outwardly from the sleeve 10 in proximity to the open end 14. The tabs 22 facilitate removal of the sleeve 10 from its container without significant risk of affecting the sterility of the inner surface 20 of the sleeve 10.

An adhesive 24 is provided on the inner surface 20 of the sleeve 10 in proximity to the open end 14 thereof. The adhesive 24 preferably is covered by a release layer or liner 26 that can be removed to expose the adhesive. The adhesive 24 is used to secure areas of the sleeve 10 adjacent the open end 14 to areas of the patient near the shoulder. The adhesive 24 preferably is selected to provide a secure attachment but easy separation from the patient. Such adhesives are well known in the art and are used for securing sterile drapes to patients in other surgical applications.

An oxygen sensor 28 (e.g., OSM) preferably is provided in the inner surface 20 of the sleeve 10 adjacent the closed end 12. A connection means can be provided for connecting the sensor 28 to an appropriate cable so that oxygen levels can be monitored during the medical procedure.

The sleeve 10 includes an opening 30 at a position between the closed end 12 and the open end 14. The opening 30 illustrated in the embodiment of FIG. 3 extends substantially linearly and substantially parallel to the longitudinal direction of the sleeve 10 from an area 30R near the wrist to an area 30B near the elbow for either radial or brachial access. The opening 30 can be defined by a perforation line or other weakened area through the plastic of the sleeve 10. Alternatively, the opening 30 can be in the form of a releasable and resealable lock, such as the types that are provided on plastic food storage bags. An adhesive 32 is provided in proximity to the opening 30 so that the inner surface 20 of the sleeve 10 can be secured to the skin of the patient near the site where catheterization will take place. The adhesive may initially be covered by a removable release liner that can be removed after the sleeve 10 is placed on the patient 1.

Figure 4:
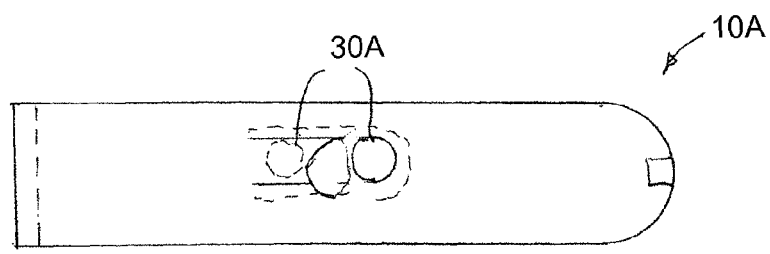
FIG. 4 is a top plan view of a variation of the sleeve of FIG. 3 in a fully expanded state.
Figure 5:
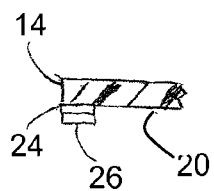
FIG. 5 is a cross-sectional view taken along line 5-5 in FIG. 3.
Figure 6:
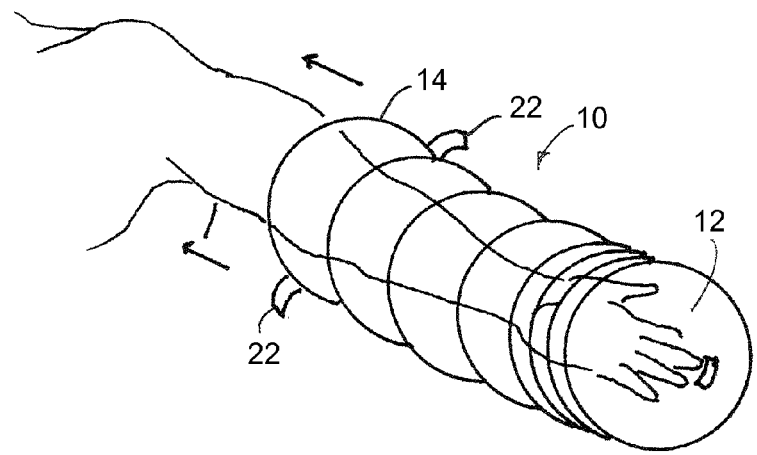
FIG. 6 is a perspective view showing the sleeve during mounting on a patient during a procedure.
Figure 7:
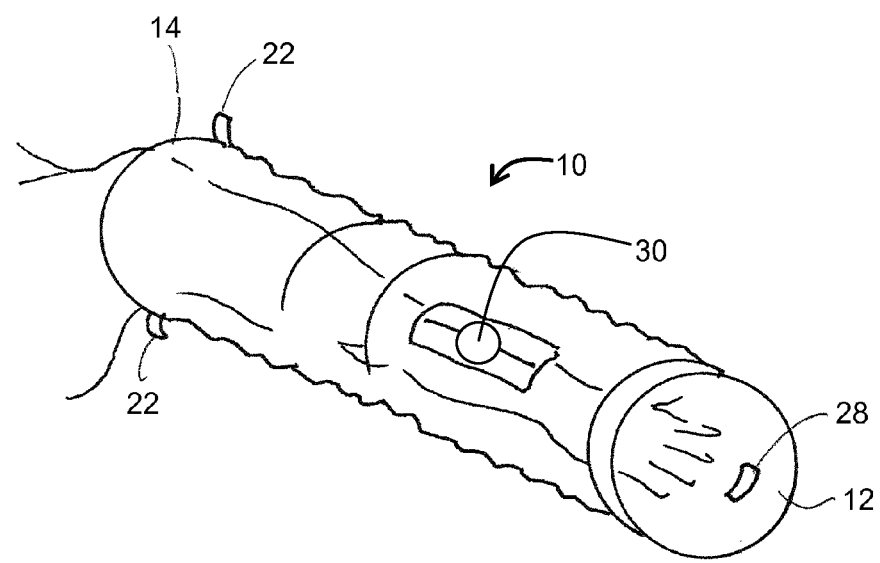
FIG. 7 is a perspective view showing the sleeve fully mounted on the patient.

FIG. 4 shows an alternate sleeve 10A that is identical to the sleeve 10 in most respects. However, the sleeve 10A has a U-shaped cut 30A to define a flap that enables access to the patient.

The sleeve 10 is employed by telescoping sleeve over the arm of the patient on the operating table and gradually expanding the collapsed sleeve so that the open end 14 can extend toward the shoulder of the patient. Health care personnel then will remove the release liner 26 from the adhesive 24 adjacent the open end 14 and will secure areas of the sleeve adjacent the open end 14 to the areas of the patient near the shoulder. The oxygen sensor 28 then is connected appropriately to a finger of the patient and an external cable is joined to the oxygen sensor 28. The doctor then separates the plastic of the sleeve 10 at the opening 30 to access the desired area for either radial or brachial catheterization. The 10 sleeve need not be spread open along the entire length of the opening 30. Rather, the doctor chooses the size needed for the appropriate location to carry out the catheterization. The release liner on the adhesive 32 near the opening 30 can be removed and the adhesive 32 then can be secured to the patient to ensure that the desired location on the patient remains accessible and to maintain sterility of that location.

The radial access catheterization sleeve described 10 above has several advantages over the prior art use of conventional sterile surgical drapes. In particular, the sleeve 10 can be mounted quickly and easily onto a patient by one health care professional. The arm of the patient is substantially completely enclosed to ensure sterility during the procedure. The adhesive around the open end 14 of the sleeve 10 facilitates secure releasable attachment to the shoulder area of the patient. Additionally, the size and shape of the sleeve 10 prevents parts of the sleeve 10 from hanging off the operating table extension in a way that could interfere with the doctor or other health care personnel working near the patient.

Figure 8:
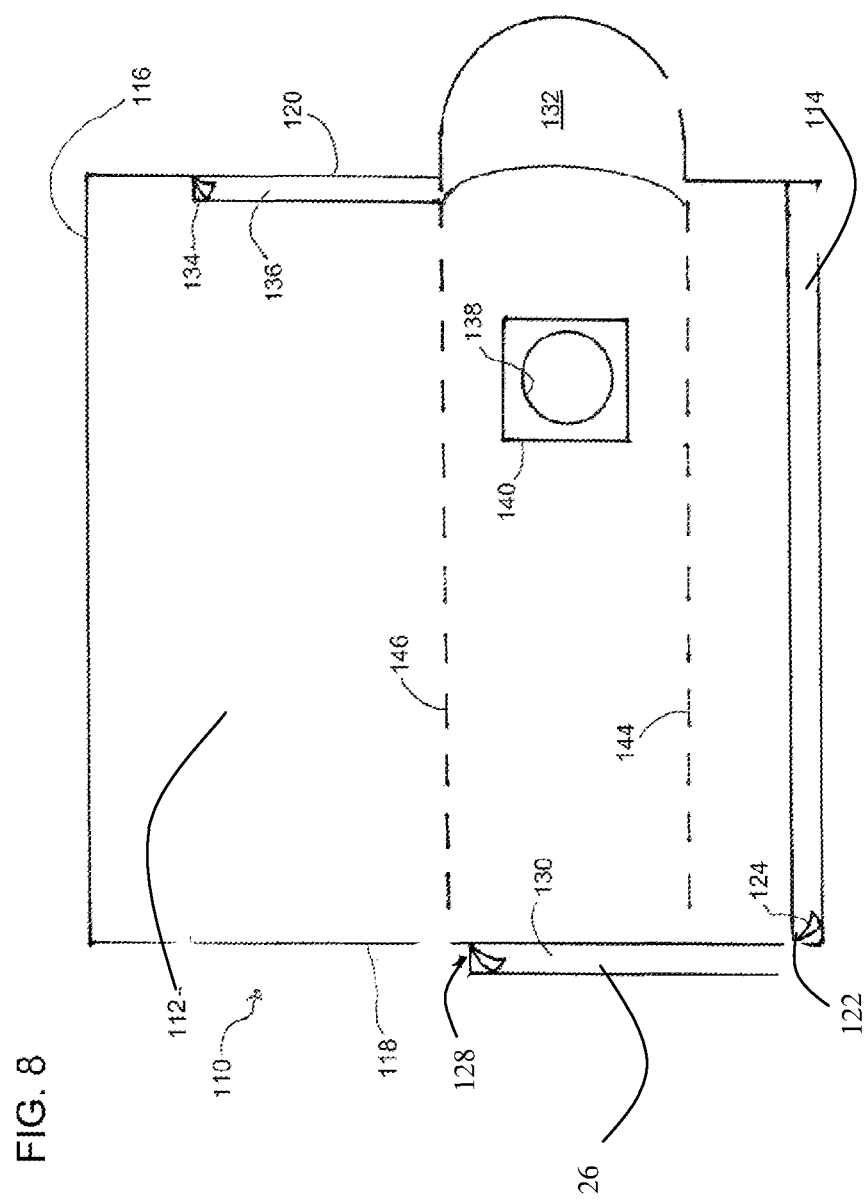
FIG. 8 is a top plan view of a sleeve in accordance with a second embodiment of the invention.
Figure 9:
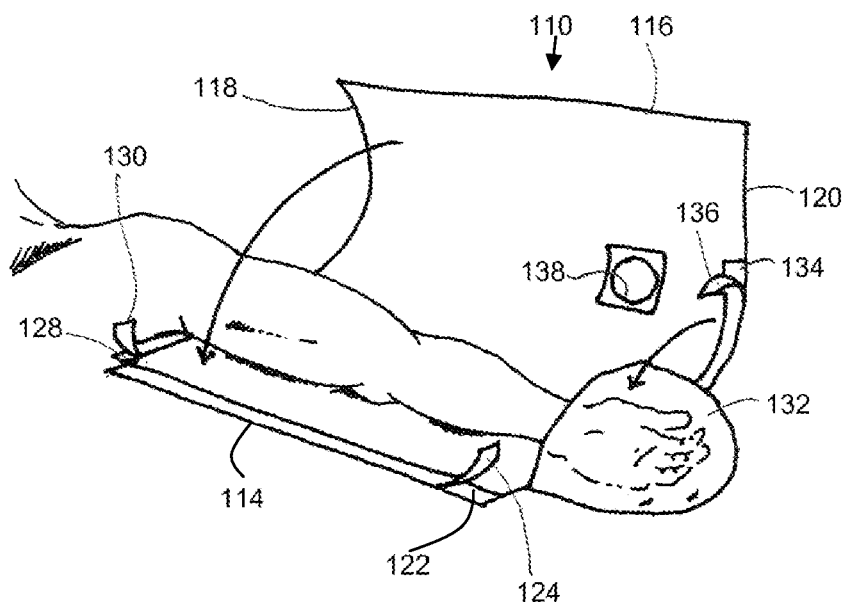
FIG. 9 is a perspective view showing the sleeve of the second embodiment during mounting on a patient.
Figure 10:
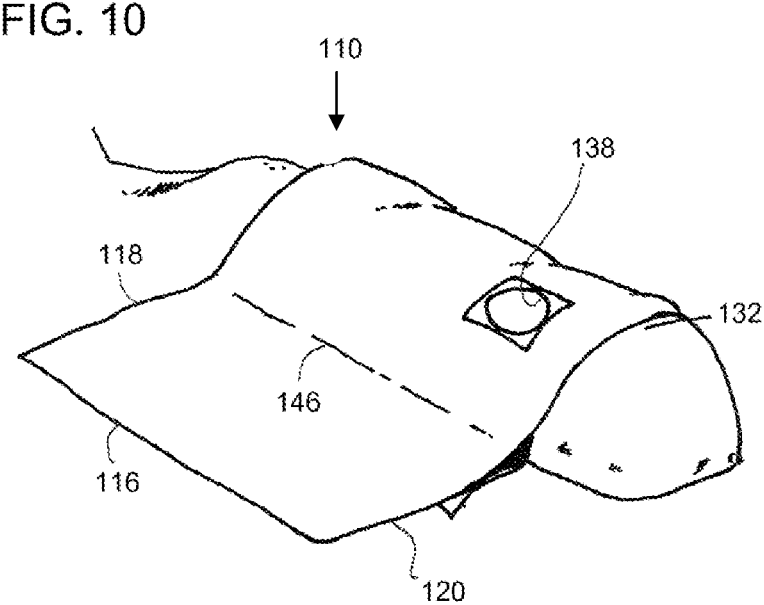
FIG. 10 is a perspective view showing the sleeve of the second embodiment fully mounted on the patient.

A radial access catheterization sleeve in accordance with a second embodiment of the invention is identified generally by the numeral 110 in FIGS. 8-10. The sleeve 110 differs from the sleeve 10 described and illustrated above primarily with respect to the initial configuration prior to mounting on the patient and the method of mounting onto the patient. However, the sleeve 110 has a shape similar to the sleeve 10 after mounting on the patient and has all of the above-described advantages. More particularly, the sleeve 110 initially is a substantially rectangular sheet 112 with opposite first and second side edges 114 and 116, a proximal edge 118 and a distal edge 120. The sheet 112 has a length of approximately 90 cm. A strip of adhesive 122 extends adjacent the first side edge 114 and is covered by a removable release liner 124. An extension 126 extends from the proximal edge 118 beginning at a position approximately 25 cm. from the adhesive strip 122 and continuing for a distance of approximately 60 cm. toward the second side edge 116. The extension 126 is provided with a layer of adhesive 128 covered by a release liner 130. A closed mitten 132 extends from the distal edge 120 and has an opening facing toward the proximal edge 118. The mitten 132 is dimensioned to accommodate a hand. More particularly, the mitten 132 defines a substantially semicircular shape with a radius of approximately 25 cm. A strip of adhesive 134 extends from the mitten 132 along the distal edge 120 toward the second side edge 116. The adhesive 134 is covered by a release liner 136. An access opening 138 is formed through the sheet 112 at a location substantially aligned with the extension 126 and the mitten 132. The access opening 138 in this embodiment is illustrated as being a circle having a diameter of approximately 5 cm. The access opening 138 is covered by a sterile closure 140 that is at least partly removable to provide access through the access opening 138. First and second fold lines 144 and 146 extend parallel to the first and second side edges 114 and 116 on opposite respective sides of the access opening 138.

The sleeve 110 of the second embodiment is employed by positioning areas of the sleeve between the first side edge 114 and the access opening 138 under the arm of the patient that will be catheterized and with the hand of the patient in the mitten 132, as shown in FIG. 9. The portion of the sheet 112 between the arm of the patient and the second side edge 116 then is folded over the arm of the patient, as shown in FIG. 9. The release liners 124, 130 and 136 can be removed at this stage. As a result, the adhesive 128 on the extension 126 from the proximal end 118 can be removably engaged with the skin of the patient at locations near the shoulder. The adhesive 134 adjacent the proximal edge 120 can be secured to the outer surface of the mitten 132. Additionally, portions of the sheet 112 near the second side edge 116 can be secured to the adhesive 122 adjacent the first side edge 114. The properly mounted sleeve 110 then is used substantially in the same manner as the sleeve 10 of the previous embodiment.

Figure 11:
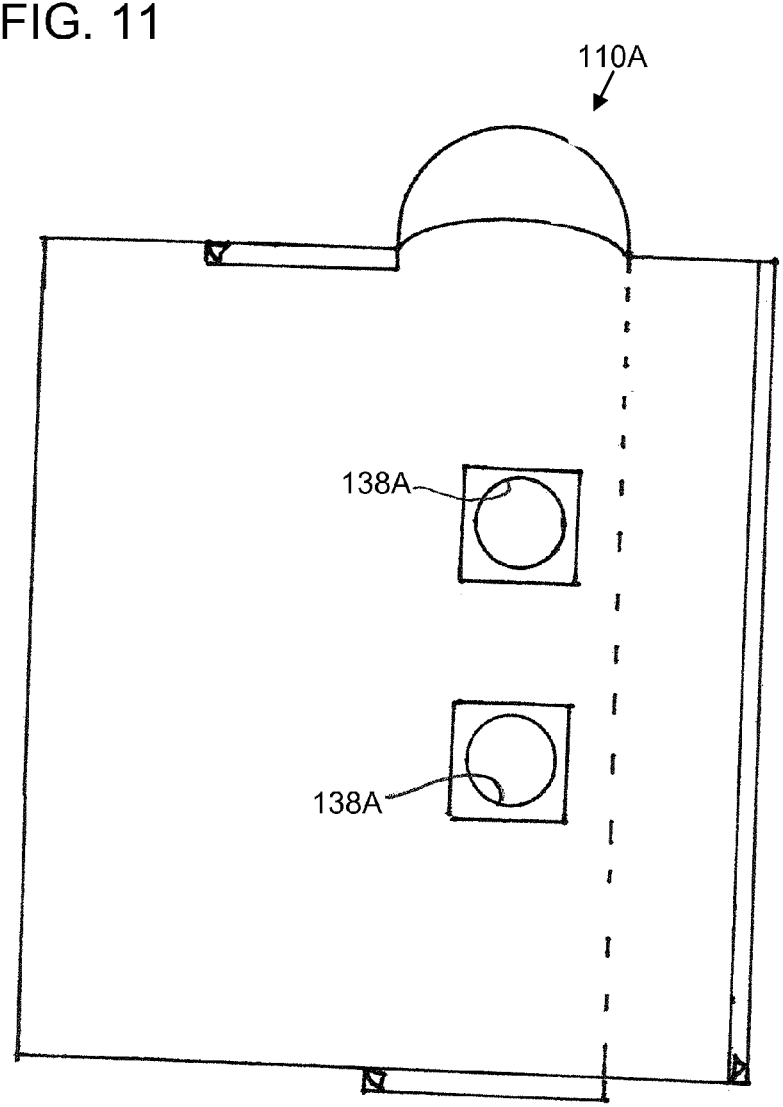
FIG. 11 is a top plan view of a sleeve in accordance with a variation of the second embodiment.

A variation of the sleeve 110 is illustrated in FIG. 11 and is identified by the numeral 110A. The sleeve 110A is identical to the sleeve 110 in most respects. However, the sleeve 110A has two access openings 138A for providing access to optional catheterization sites in the arm of the patient.

Figure 12:
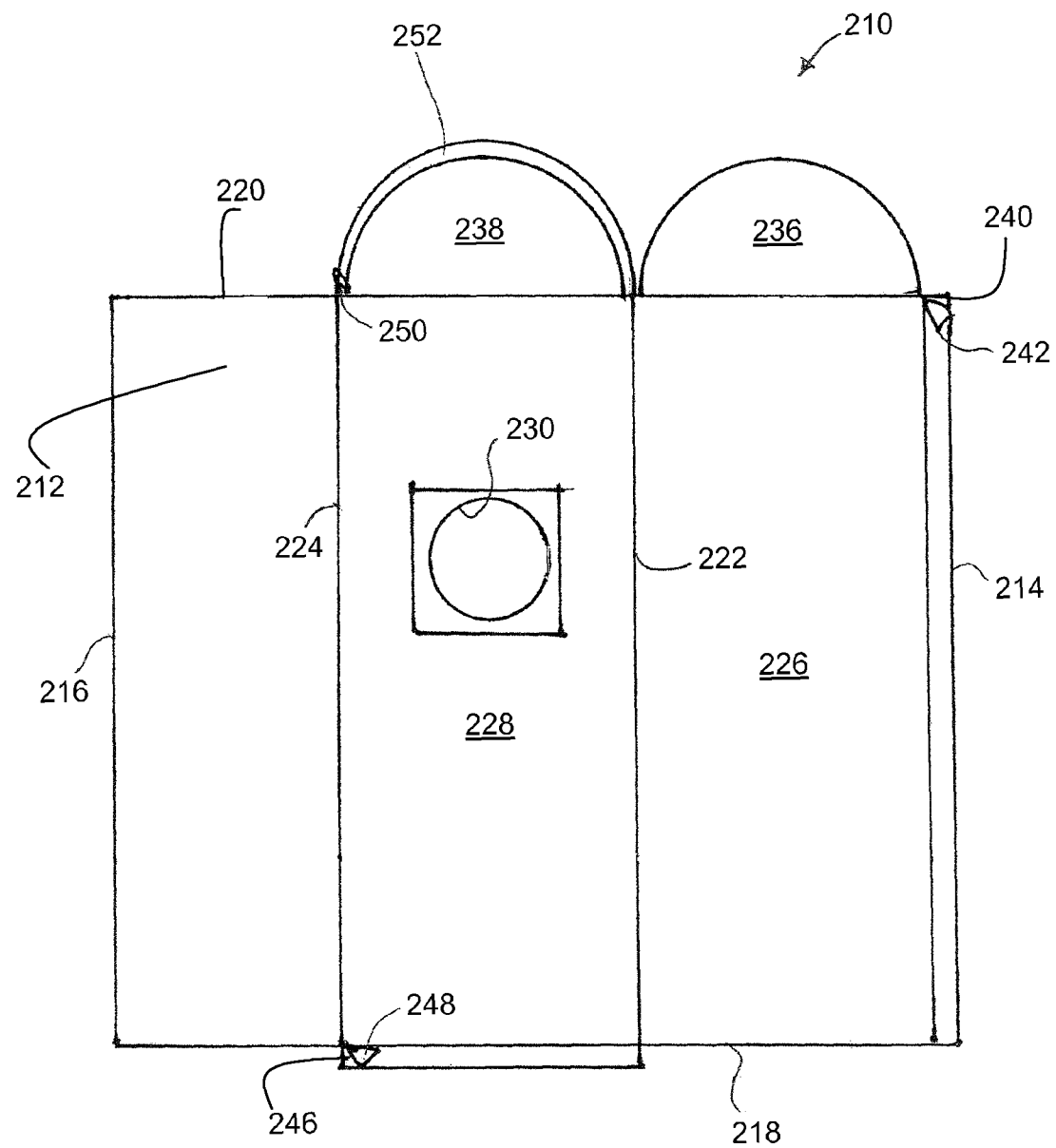
FIG. 12 is a top plan view of a sleeve in accordance with a third embodiment of the invention.
Figure 13:
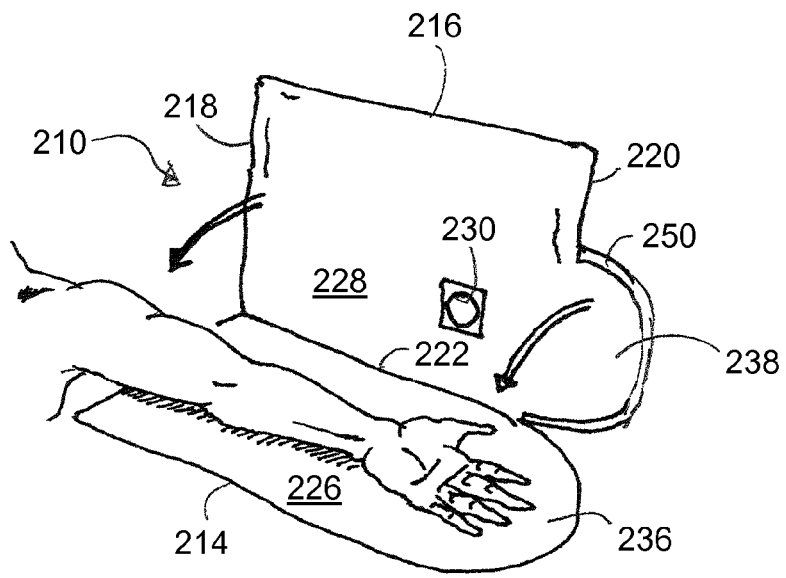
FIG. 13 is a perspective view showing the sleeve of the third embodiment during mounting on a patient.
Figure 14:
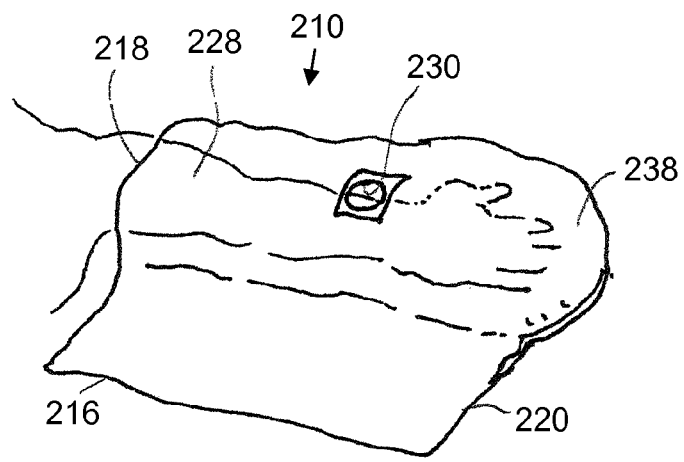
FIG. 14 is a perspective view showing the sleeve of the third embodiment fully mounted on the patient.

A third embodiment of the invention is identified generally by the reference numeral 210 in FIGS. 12-14. The sleeve 210 is similar to the sleeve 110 described and illustrated above. However, the sleeve 210 does not have a preformed mitten. More particularly, the sleeve 210 is formed from a generally rectangular sheet 212 having opposite first and second side edges 214 and 216, a proximal edge 218 and a distal edge 220. First and second longitudinally extending fold lines 222 and 224 extend substantially parallel to the first and second side edges 214 and 216. The first fold line 222 is spaced from the first side edge 214 by approximately 60 cm. and a bottom panel 226 is defined between the first side edge 214 and the first fold line 222. The first and second fold lines 222 and 224 are spaced from one another by approximately 60 cm and define a top panel 228 therebetween. An access opening 230 extends from the second fold line 224 to the second side edge 216. The access opening 230 is formed in the top panel 228 substantially as described with respect to the previous embodiments. More particularly, the access opening 230 may be covered by a releasable panel and may be surrounded at least partly by an adhesive that can be secured to the skin of the patient at areas surrounding the location of catheterization. Bottom and top semicircular extensions 236 and 238 extend from the distal edge 220 at locations aligned respectively with the bottom and top panels 226 and 228. The semicircular extensions 236 and 238 each have a radius of approximately 25 cm. A strip of adhesive 240 extends adjacent the first side edge 214 and is covered by a release liner 242. An extension extends proximally from the top panel 228 and has a layer of adhesive 246 covered by a release liner 248 thereon. Additionally, a layer of adhesive 250 covered by a release liner 252 extends around the curved edge of the semicircular top extension 238.

Figure 15:
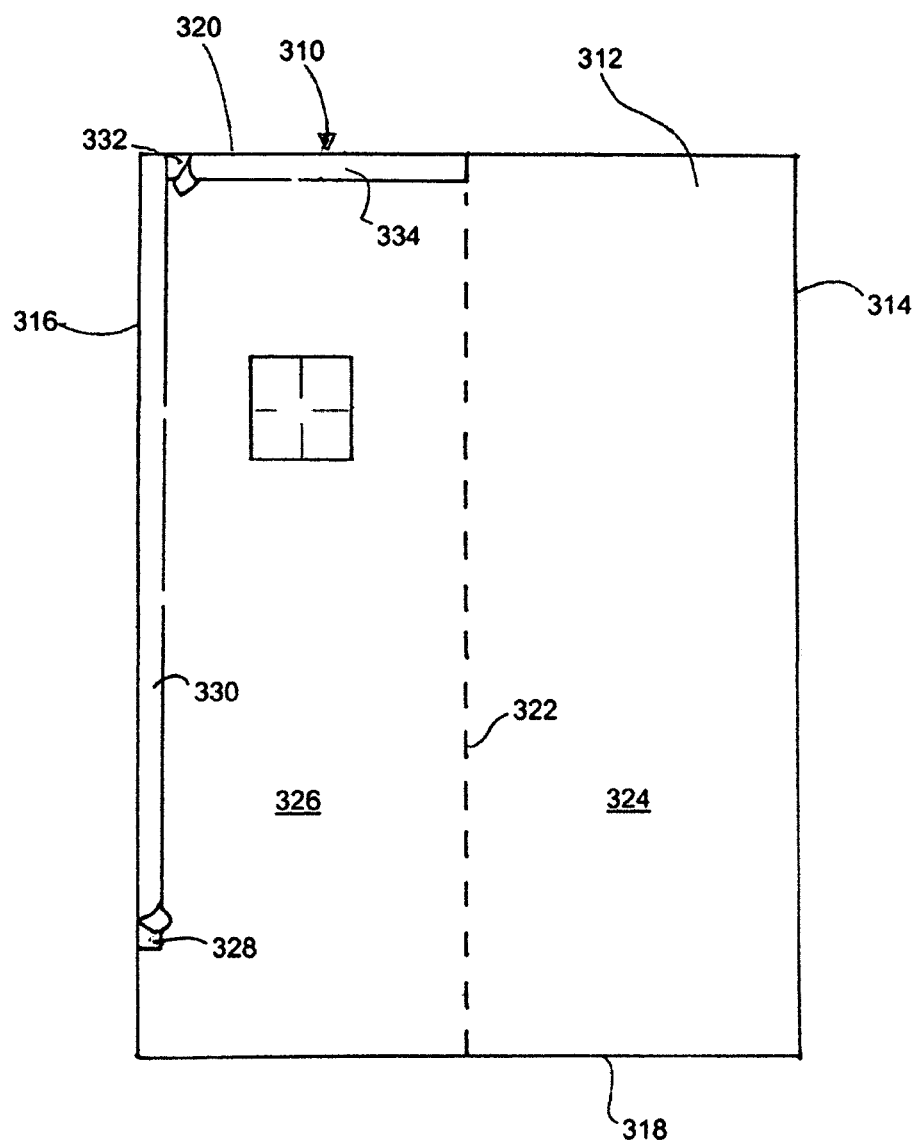
FIG. 15 is a top plan view of a sleeve in accordance with a fourth embodiment of the invention.

A sleeve in accordance with a fourth embodiment of the invention is identified generally by the reference numeral 310 in FIG. 15. The sleeve 310 includes a rectangular sheet 312 having first and second side edges 314 and 316, a proximal edge 318 and a distal edge 320. A fold line 322 extends the length of the sheet 312 from the proximal edge 318 to the distal edge 320 and is aligned substantially parallel to the side edges 314 and 316. Thus, a bottom panel 324 is defined between the first side edge 314 and the fold line 322, and a top panel 326 is defined between the fold line 322 and the second side edge 316. An adhesive strip covered by a release liner 330 extends substantially along the second side edge 316. Additionally, an adhesive strip 332 covered by a release liner 334 extends along portions of the distal edge 320 aligned with the top panel 326. An access opening 336 is formed in the top panel 326 approximately centrally between the fold area 322 and the second side edge 316. The access opening 336 is closer to the distal edge 320 than the proximal edge 318, and preferably is about 10 inches from the proximal edge 318.

A sleeve in accordance with a fourth embodiment of the invention is identified generally by the reference numeral 310 in FIG. 15. The sleeve 310 includes a rectangular sheet 312 having first and second side edges 314 and 316, a proximal edge 318 and a distal edge 320. A fold line 322 extends the length of the sheet 312 from the proximal edge 318 to the distal edge 320 and is aligned substantially parallel to the side edges 314 and 316. Thus, a bottom panel 324 is defined between the first side edge 314 and the fold line 322, and a top panel 326 is defined between the fold line 322 and the second side edge 316. An adhesive strip 328 covered by a release liner 330 extends substantially along the second side edge 316. Additionally, a distal adhesive strip 332 covered by a release liner 334 extends along portions of the distal edge 320 aligned with the top panel 326. An access opening 336 is formed in the top panel 326 approximately centrally between the fold area 322 and the second side edge 316. The access opening 336 is closer to the distal edge 325 than the proximal edge 318, and preferably is about 10 inches from the proximal edge 320.

The sleeve 310 is used in a manner similar to the sleeves 110 and 210 described above. More particularly, the bottom panel 324 is positioned under the arm of the patient as shown in FIG. 16. The top panel 326 then is folded about the fold area 322. The release liners 330 and 334 can be removed so that the adhesive 332 adjacent the distal edge 320 can be secured to areas of the bottom panel 324 adjacent the distal edge 320. Similarly, the adhesive 328 can be secured to areas of the bottom panel 324 substantially adjacent the first side edge 314. With this arrangement, the access opening 336 is positioned adjacent the desired catheterization location on the arm of the patient, as shown most clearly in FIG. 17.

A radial access catheterization sleeve in accordance with a fifth embodiment of the invention is identified by the numeral 410 in FIGS. 16-20. The sleeve 410 of the fifth embodiment has a closed end 412, an open end 414 and a generally tubular side wall 416 extending between the ends. The tubular side wall 416 has opposite inner and outer surfaces 418 and 420. Opposed slits 422 extend from the open end 414 part of the distance toward the closed end 412. An adhesive 424 is provided on the inner surface 420 of the sleeve 410 adjacent the slits 422. The adhesive 424 preferably is covered by a release layer or liner 426 that can be removed to expose the adhesive 424. The adhesive 424 is used to secure areas of the sleeve 410 adjacent the medially disposed slit 422 to areas of the patient near the shoulder. The adhesive 424 adjacent the slit 422 that is laterally disposed can be used to secure the slit 422 closed. The adhesive preferably is selected to provide a secure attachment but easy separation from the patient.

The sleeve 410 includes a sterile opening 428 that is covered in a sterile manner by a protective sheet 430 that is selectively removable from the sleeve 410 to expose the skin of the patient's arm. A flap 432 is mounted hingedly to the sleeve 410 at a permanent hinge line 433 in proximity to both the sterile opening 428 and the removable protective sheet 430. The flap 432 includes a small access opening 434 and an adhesive 436 at least partly surrounds the access opening 434. A protective release layer 438 is attached removably to the flap 432 for covering the access opening 434 and covering and protecting the adhesive 436 around the access opening 434.

The protective sheet 430 may be removed after the sleeve 410 is mounted on the patient to expose the skin of the patient near the blood vessel that will be entered. The release layer 438 then may be removed from the flap 432 and the flap 432 may be rotated about the hinge line 433 and relative to the sleeve 410 to overlie the sterile opening 428 in the sleeve 410 that had been covered by the protective sheet 430. The adhesive 436 that surrounds the access opening 434 in the flap 432 may be secured to the outer surface 420 of the sleeve 410 near the sterile opening 428 or adhered to the skin of the patient near the sterile opening 428. The radial access catheterization then may be carried out in a conventional manner The above-described embodiments are one examples of the disposable radial or brachial access catheterization sleeve in accordance with the invention. Openings of different sizes or shapes can be provided in addition to the alternates illustrated herein. Other means for closing the openings also can be provided. Additionally, the oxygen saturation monitor can be omitted in certain less preferred embodiments. The proximal edge of the sleeve is configured as being aligned perpendicular to a longitudinal direction of the sleeve. However, the proximal end can be aligned at an acute angle to the longitudinal direction to nest more securely at the shoulder of the patient. Although only one sleeve is illustrated, sleeves may come in a plurality of different sizes. Furthermore, the sleeve can be packaged with and used with a small sterile sheet that can be used to reduce the size of the opening in the sleeve.

What is claimed is:

1. A sterile catheterization sleeve for use during a surgical procedure, comprising:
    a rectangular sheet that includes opposite proximal and distal edges and opposite first and second side edges that connect the opposite proximal and distal edges, wherein the rectangular sheet includes a bottom panel and a top panel connected to the bottom panel along a fold line;
    an access opening formed in the bottom panel between the proximal and distal edges of the rectangular sheet, and between the first and second side edges of the rectangular sheet, wherein the access opening is completely surrounded by the rectangular sheet;
    a removable sterile closure that covers the access opening;
    a first adhesive strip formed along a first portion of the distal edge of the rectangular sheet;
    a second adhesive strip formed along the first side edge of the rectangular sheet; and
    a semicircular mitten that extends from the bottom panel and a second portion of the distal edge of the rectangular sheet adjacent to the first adhesive strip, wherein the distal edge is between the semicircular mitten and the access opening,
    wherein the semicircular mitten includes a semicircular lower panel and a semicircular upper panel,
    wherein the rectangular sheet is configured to be folded along the fold line into a closed configuration, wherein the bottom panel is secured to the top panel by the second adhesive strip and the top panel is secured to the semicircular mitten by the first adhesive strip.

2. The catheterization sleeve of claim 1, further comprising a third adhesive strip formed along the proximal edge on the bottom panel, wherein the third adhesive strip is configured to adhere to a limb of a patient when the rectangular sheet is folded into the closed configuration about the patient's limb.

3. The catheterization sleeve of claim 1, wherein the semicircular mitten includes the semicircular lower panel unitary with the bottom panel and the semicircular upper panel is attachable to the top panel.

* * * * *